(12) United States Patent
Gruber

(10) Patent No.: US 9,000,033 B2
(45) Date of Patent: Apr. 7, 2015

(54) COMPOSITION FOR IMPROVING SKIN CONDITION AND APPEARANCE

(75) Inventor: James V Gruber, Washington, NJ (US)

(73) Assignee: Arch Personal Care Products, L.P., South Plainfield, NJ (US)

( * ) Notice: Subject to any disclaimer, the term of this patent is extended or adjusted under 35 U.S.C. 154(b) by 763 days.

(21) Appl. No.: 12/512,368

(22) Filed: Jul. 30, 2009

(65) Prior Publication Data

US 2010/0143451 A1 Jun. 10, 2010

Related U.S. Application Data

(60) Provisional application No. 61/085,114, filed on Jul. 31, 2008.

(51) Int. Cl.
| | | |
|---|---|---|
| A61K 9/127 | (2006.01) | |
| A61K 31/352 | (2006.01) | |
| A61K 9/14 | (2006.01) | |
| A61Q 19/08 | (2006.01) | |
| A61K 8/11 | (2006.01) | |
| A61K 8/49 | (2006.01) | |
| A61K 8/97 | (2006.01) | |

(52) U.S. Cl.
CPC . *A61Q 19/08* (2013.01); *A61K 8/11* (2013.01); *A61K 8/498* (2013.01); *A61K 8/97* (2013.01)

(58) Field of Classification Search
None
See application file for complete search history.

(56) References Cited

U.S. PATENT DOCUMENTS

| 2,752,314 | A | 6/1956 | Clopton et al. |
|---|---|---|---|
| 4,254,105 | A | 3/1981 | Fukuda |
| 4,960,764 | A | 10/1990 | Figueroa, Jr. et al. |
| 5,605,894 | A | 2/1997 | Blank et al. |
| 6,093,411 | A | 7/2000 | Bissett |
| 7,348,034 | B2 | 3/2008 | Murray et al. |
| 7,351,745 | B2 | 4/2008 | Dryer et al. |
| 2001/0020009 | A1 | 9/2001 | Nair et al. |
| 2003/0125264 | A1 | 7/2003 | Malik |
| 2003/0198682 | A1 | 10/2003 | Gruber et al. |
| 2008/0119433 | A1 | 5/2008 | Tabor |

FOREIGN PATENT DOCUMENTS

| JP | 05213735 | 8/1993 |
|---|---|---|
| JP | 7118151 A | 5/1995 |
| JP | 2006193512 A | 7/2006 |
| JP | 2007176816 A | 7/2007 |
| WO | WO 97/39733 | 10/1997 |
| WO | 0013661 | 3/2000 |
| WO | WO 2006/033987 | 3/2006 |

OTHER PUBLICATIONS

Tahara, et al. (1995) "Prenylated Isoflavonoids—An Update", Phytochemistry, 38(5): 1073-94.*
Gygi (1999) "Correlation between Protein and mRNA Abundance in Yeast", Molecular and Cellular Biology, 19(3): 1720-30.*
Fulton, et al. (2008) "Crystal structure of a UDP-glycose-specific Glycosyltransferase from a Mycobacterium species" Journal of Biological Chemistry, 283(41): 27881-90.*
Tian, et al. (2006) "Phenylpropanoid glycosyltransferases from osage orange (Maculara pomifera) fruit", FEBS Letters, 6915-20.*
Svasti J et al., Proteomic profiling of cholangiocarcinoma cell line treated with pomiferin from Derris malaccensis. Proteomics 5 (2005) 4504-4509.
Li H, Yang M, Ma X. Zhongguo Zhong, Yao Za Zhi Mar. 2009;34(6):724-6 Flavonoids from roots of Flemingia philippinensis. (abstract only).
Shiao YJ, Wang CN, Wang Wy, Lin YL. Planta Med. Sep. 2005;71(9):835-40. Neuroprotective flavonoids from Flemingia macrophylla.
Galicka et al. "Stimulation of collagen biosynthesis by flavonoid glycosides in skin fibroblasts of osteogeneis imperfecta type I and the potential mechanism of their action", International Journal of Molecular Medicine 20: pp. 889-895, 2007.
Tsao et al. "Antioxidant Isoflavones in Osage Orange, Maclura pomifera (Raf) Schneid", J. Agric. Food Chem. 2003, 51, pp. 6445-6451.
Hamed et al. "Effect of Maclura pomifera total acetonic extract, pomiferin and osajin on the autooxidation of purified sunflower triacylglycerols", Grasas y Aceites, vol. 56. Fasc 1 (2005), pp. 21-24.
Marek et al. "Pomiferin", Acta Cryst. (2003) C59, pp. o127-o128.
Vesela et al. "Antioxidative and EROD activities of osajin and pomiferin", Fitoterapia 75 (2004) pp. 209-211.
Liskova et al. "Osajin", Acta Cryst (2005) E61, pp. o1848-o1850.
Mahmoud, Zeinab F., "Antimicrobial Components from Maclura pomifera Fruit" Journal of Medicinal Plant Research. vol. 42: 299-301, 1981.
Choi, Eun-Mi, "The licorice root derived isoflavan glabridin increases the function of osteoblastic MC3t3-E1 cells" Biochemical Pharmacology. vol. 70: 363-368, 2005.
Extended European Search Report dated Nov. 19, 2014, issued in counterpart European Application No. 09 80 3624.

* cited by examiner

*Primary Examiner* — Robert M Kelly
(74) *Attorney, Agent, or Firm* — Miles and Stockbridge

(57) ABSTRACT

Disclosed is a cosmetic composition comprising prenylated isoflavonoid and a carrier, wherein the prenylated isoflavonoid is from about 0.0000001% to about 10%, preferably from 0.00001% to 1%, most preferably from 0.01% to 1%, by weight, based on the total weight of the composition. The active agent prenylated isoflavonoid induces a statistically significant upregulation of collagen 1A1 and elastin genes in normal human dermal fibroblasts. The composition is effective to stimulate the production of collagen and elastin and improve the appearance and condition of the skin.

13 Claims, 3 Drawing Sheets

COMPOSITION FOR IMPROVING SKIN CONDITION AND APPEARANCE

CROSS REFERENCE TO RELATED APPLICATIONS

This application claims the benefit of U.S. Provisional Patent Application Ser. No. 61/085,114, filed on Jul. 31, 2008, the disclosure of which is incorporated herein by reference in its entirety.

FIELD OF INVENTION

The present invention generally relates to compositions for improving skin condition and appearance, and more particularly to cosmetic compositions including prenylated isoflavonoid compounds effective for inducing a statistically significant upregulation of genes in normal human dermal fibroblasts. The present invention also relates to methods for regulating skin condition.

BACKGROUND OF THE INVENTION

Though many things contribute to a younger, healthier appearance, one of the most important is a fibrous protein called collagen. Collagen, especially collagen 1A1 connects and supports skin tissues. It works hand-in-hand with another fibrous protein, elastin. Basically, collagen provides the skin its form and firmness; elastin gives the same skin elasticity and flexibility. In addition, the skin produces other fibrous proteins that provide important linkages to the skin cells. For example, fibrillin protein is expressed in the skin and is intimately associated with elastin, surrounding amorphous elastin filaments and providing additional structure and strength.

As people age, the skin losses collagen because the body gradually produces less and less collagen. In addition, other factors, such as UV light may also contribute to the loss of collagen because these factors may trigger an increased production of proteolytic enzymes that break down collagen. The reduction of collagen and elastin in the skin leads to the appearance of fine lines, wrinkles, age spots, and sagging skin.

Some cosmetic compositions having active agents that supposedly help stimulate collagen production by the body have been disclosed.

U.S. Pat. No. 7,351,745, which is incorporated herein by reference in its entirety, discloses a cosmetic composition containing one or more active agents selected from the group consisting of: L-Theanine, S-Methyl-L-Cysteine, S-phenyl-L-Cysteine. According to the patent, the active agents are found effective to increase expression levels of at least one gene selected from the group consisting of collagen 4, collagen 7 and a few other genes.

U.S. Pat. No. 7,348,034 discloses a cosmetic composition that allegedly works by increasing the synthesis of collagen or elastin and/or preventing or slowing the degradation of collagen and elastin. The composition includes grape seed extract, wolfberry extract, and rosehip. U.S. Pat. No. 7,348,034 is incorporated herein by reference in its entirety.

In spite of these disclosures, there is still a need for active agents that are effective to stimulate the production of collagen and elastin, thus improving the condition and appearance of the skin.

Flavonoids are a class of plant pigments. They are best known for their antioxidant activities. Certain flavonoids have been used in topical compositions.

U.S. Pat. No. 6,093,411 discloses that certain selected flavonoid compounds can be used to prevent or treat skin disorders. The active agent is selected from isoflavones, coumarins, chromones, dicoumarols, chromanones and chromanols.

U.S. Publication 2003/0125264 discloses that flavones, flavonols, flavanones, isoflavanones and isoflavones may be used in the treatment of wounds by increasing proliferation of fibroblast cells.

It has now been surprisingly found that certain prenylated isoflavonoid compounds are effective for inducing a statistically significant upregulation of collagen 1A1 and elastin genes in normal human dermal fibroblasts.

It is therefore an object of the present invention to provide topical compositions containing an appropriate amount of a particular class of isoflavonoid compounds for improving skin condition and appearance.

It is another object of the present invention to provide methods of regulating skin by using the subject compositions.

These and other objects of this invention will become apparent in light of the following disclosure.

SUMMARY OF THE INVENTION

In one aspect, the present invention relates to a composition having active agents effective to increase collagen 1A1 and elastin gene expression in normal human dermal fibroblasts. The composition comprises a prenylated isoflavonoid and a cosmetically or determatologically acceptable carrier, where the prenylated isoflavonoid is from 0.0000001% to 10%, preferably from 0.00001% to 1%, most preferably from 0.01% to 1% and the carrier is from about 50% to about 99%, preferably from about 75% to about 99%, based on the total weight of the composition. The prenylated isoflavonoid is selected from the group consisting of pomiferin, osajin and a combination thereof.

In another aspect, the present invention relates to a method for regulating skin condition by using a composition containing a safe and effective amount of prenylated isoflavonoid and an acceptable carrier.

BRIEF DESCRIPTION OF THE DRAWINGS

The invention will be more fully understood from the following detailed description taken in conjunction with the accompanying drawings, in which.

DETAILED DESCRIPTION OF THE PREFERRED EMBODIMENTS

Figure 1:
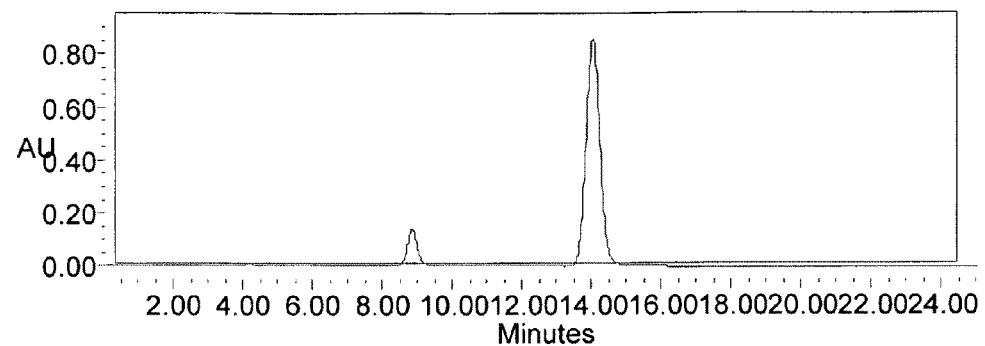
FIG. 1 is a graph showing HPLC analysis results of osajin standard.

The present invention relates to a topical composition having one or more active agents that improve the appearance and condition of the skin by controlling the extracellular matrix proteins of the skin, especially collagen and elastin. The invention is based on the surprising discovery that an appropriate amount of prenylated isoflavoid induces a statistically significant upregulation of collagen 1A1 and elastin genes in normal human dermal fibroblasts.

Fibroblasts are cells that grow in the dermal layer of the skin that are responsible for expression of new collagen and elastin into the skin. Such cells can be grown in culture dishes under conditions known as in vitro to examine beneficial influences of topical treatments. The prenylated isoflavonoids of the present invention may also act on other cells known to exist in the skin such as, but not limited to, keratinocytes, melanocytes, nerve cells, immune cells, adipocytes and the like. In addition, the preneylated isoflavonoids of the present invention may affect cells such as dermal papillae cells, sebocytes, stem cells and the like. The prenylated isoflavonoids of the present invention may also act on the stratum corneum of the skin, a portion of the skin which is essentially non-living but which is non-the-less susceptible to the effects of free radicals and solar radiation damage.

The expression of collagen and elastin can be measured in multiple ways using in vitro assays, but two very practical methods are by human gene microarrays and by Enzyme-Linked Immunosorbent Assays (ELISA). The microarray technique employs genomic microchips such as those provided by Affymetrix (Santa Clara, Calif.) to examine whether a particular treatment influences the fibroblast's genetic predisposition to create collagen or elastin by increasing or decreasing RNA expression. The ELISA test examines the actual expression of collagen or elastin by using fluorescently-labeled antibodies specific for the particular protein of interest. Typically, if a treatment upregulates a fibroblast's gene expression of collagen 1A1 and elastin, then the treatment will likely increase expression of the collagen 1A1 and elastin proteins as well.

It is found for the first time that an appropriate amount of one or more prenylated isoflavonoids, particularly osajin and pomiferin, significantly increase expression levels of collagen 1A1 and elastin genes. For example, studies show that when treated with 0.05% pomiferin, normal human dermal fibroblasts show a statistically significant increase in collagen 1A1 and elastin gene expression compared to untreated cells. Further studies demonstrate that pomiferin at a concentration from 0.0001 to 0.05% is equally effective in increasing collagen 1A1 and elastin gene expression.

Thus, the present invention provides a composition containing a safe and effective amount of prenylated isoflavonoid(s) and a carrier. The composition is effective in stimulating the production of collagen and elastin of the skin when applied to the skin under normal treatment conditions. The composition of the present invention is also effective in treating, preventing, and ameliorating the appearance of fine lines, wrinkles, age spots, sagging and other unhealthy skin conditions associated with the loss of collagen and elastin. The prenylated isoflavonoids of the present invention is also effective at modulating skin color or tone and for reducing inflammatory responses in the skin.

For the purpose of the present invention, the prenylated isoflavonoid is present in an amount of 0.0000001%-10.0%, preferably in an amount of 0.00001%-1%, more preferably in an amount of 0.01%-1%, based on the total weight of the composition.

Essential Components
Prenylated Isoflavonoid Compounds

An essential ingredient of the compositions of the present invention is a prenylated isoflavonoid of the general structure shown below:

General Prenylated Isoflavonoid Structure

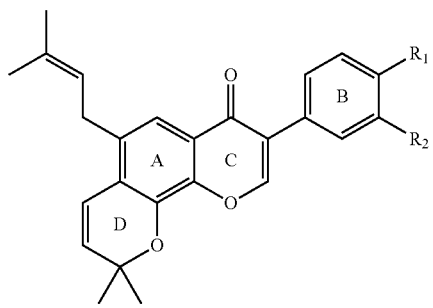

Formula I

Prenylated isoflavonoids differ from simple isoflavonoids such as are disclosed, for example, in U.S. Pat. No. 6,093,411 issued to Bissett which have the general structure shown below:

General Isoflavonoid Structure

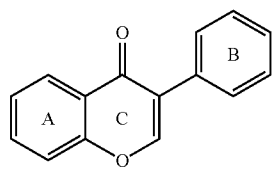

Formula II

The prenylated isoflavonoids differ from simple isoflavonoids by containing an additional cyclic ring structure, D, and by having an additional terpene moiety attached to ring A that is absent from the simple isoflavonoids of U.S. Pat. No. 6,093,411.

Prenylated isoflavonoids also differ from simple flavonoids such as are disclosed, for example, in US 2001/0020009 issued to Nair et al., which also lack the additional six-membered ring, D, the attached terpene on ring A and also by having a differing stereochemistry between ring B and ring C than the prenylated isoflavonoids.

General Flavonoid Structure

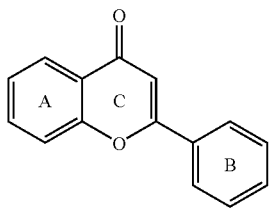

Formula III

The prenylated isoflavonoids of the present invention can be synthetic materials or obtained as extracts from natural sources (e.g., plants). Of particular interest are the prenylated isoflavonoids isolated from extracts of the plant *Maclura*

*pomifera* (Common name: Osage orange). Extracts of the fruit of this plant have been reported to contain two unique prenylated isoflavonoids known as pomiferin ($R_1=R_2=OH$) and osajin ($R_1=OH$, $R_2=H$). The chemical structures of these two prenylated isoflavonoids have been established [Pomiferin: Marek J et al., Acta Cryst (2003) C59, o127-o128, Osajin: Liskova M et al., Acta Cryst (2005) E61, o1848-o1850]. The isolation of these two prenylated isoflavonoids and their general antioxidant properties have been previously reported [Tsao R et al., J Agric Food Chem (2003) 51, 6445-6451 and Vesela D et al, Fitoterapia (2004) 75, 209-211 and Hamed S F et al., Grasas y Aceites (2005) 56, 21-24].

US Patent Application WO 2006/033987 suggested that ethanolic extracts of Osage Orange heartwood may have inhibitory activity on melanin synthesis including potential applications for skin lightening. However, this patent fails to mention the unique prenylated isoflavonoids osajin and pomiferin and chromatographic analysis provided by the inventors does not indicate the presence of either pomiferin or osajin in the heartwood extracts. In addition, extracts of the heartwood of trees are known to contain sap which can contain undesirable organic chemicals that can irritate human skin.

Solvents used for extracting the prenylated isoflaovanoids from Osage orange are known to those skilled in the art and include, but are not limited to, aqueous extraction, aqueous-alcoholic extraction, aqueous-glycol extraction, organic solvent extraction, supercritical carbon dioxide extraction, liquid propane or liquid butane extraction, and the like. Methods of extraction can include, but are not limited to, simple solvent extraction, pressurized hot water extraction, steam extraction, counter current extraction, gaseous extraction and the like.

In addition, the extracts may be subjected to further downstream processes including, but not limited to chromatography, vacuum distillation, freeze drying, drum drying, cyclone drying, spray drying, carbon treatment, plate-and-frame filtration, high pressure filtration, centrifugation, and the like. The extracts may be further treated to encapsulate them either in lipid encapsulants such as, for example, liposomes, or polymer encapsulants such as, for example, maltodextrins. The extracts may be encapsulated in polymeric matrix, niasome and nanoparticles.

The naturally sourced material can also further be derivatized (e.g., an ester or ether derivative prepared following extraction from a natural source). Flavonoid compounds useful herein are commercially available from commercial sources such as, Gaia Chemical Company (Gaylordsville, Conn.). The prenylated isoflavonoids may also be used for a portion of an additional fermentation process media either in the solid state or as part of a liquid fermentation process with other microorganisms such as, for example, *Saccharomyces, Lactobacillus,* or *E. coli*.

Carrier

Another essential ingredient of the present invention is a cosmetically or dermatologically-acceptable carrier for prenylated isoflavonoids. The carrier is not limited to any particular form. The exemplary carriers are water, oil, water-in-oil, oil-in-water, oil-in-water-in-silicon emulsions. A detailed discussion of suitable carriers may be found in U.S. Pat. No. 6,093,411. The patent is hereby incorporated by reference in its entirety.

The carriers of the present invention can comprise from about 50% to about 99% by weight of the compositions of the present invention, preferably from about 75% to about 99%, and most preferably from about 85% to about 95%.

Optional Components

The skin regulating compositions of the present invention may optionally comprise additional skin actives and other components depending on the carrier. A more detailed discussion of suitable additional skin actives and other components may be found in U.S. Pat. No. 6,093,411, the disclosure of which is incorporated herein in its entirety.

Non-limiting examples of such skin actives include vitamin B3 compounds such as those described in PCT application WO 97/39733, published Oct. 30, 1997, to Oblong et al., herein incorporated by reference in its entirety; hydroxy acids such as salicylic acid; exfoliation or desquamatory agents such as zwitterionic surfactants; sunscreens such as 2-ethylhexyl-p-methoxycinnamate, 4,4'-t-butyl methoxydibenzoylmethane, octocrylene, phenyl benzimidazole sulfonic acid; sun-blocks such as zinc oxide and titanium dioxide; anti-inflammatory agents; anti-oxidants/radical scavengers such as tocopherol and esters thereof; metal chelators, especially iron chelators; retinoids such as retinol, retinyl palmitate, retinyl acetate, retinyl propionate, and retinal; N-acetyl-L-cysteine and derivatives thereof; hydroxy acids such as glycolic acid; keto acids such as pyruvic acid; benzofuran derivatives; depilatory agents (e.g., sulfhydryl compounds); skin lightening agents (e.g., arbutin, kojic acid, hydroquinone, ascorbic acid and derivatives such as ascorbyl phosphate salts, placental extract, and the like); anti-cellulite agents (e.g., caffeine, theophylline); moisturizing agents; anti-microbial agents; anti-androgens; and skin protectants. Mixtures of any of the above mentioned skin actives may also be used. A more detailed description of these actives is found in U.S. Pat. No. 5,605,894 to Blank et al. (previously incorporated by reference). Preferred skin actives include hydroxy acids such as salicylic acid, sunscreen, antioxidants and mixtures thereof.

Other conventional skin care product additives may also be included in the compositions of the present invention. For example, urea, guanidine, glycerol, petrolatum, mineral oil, sugar esters and polyesters, polyolefins, methyl isostearate, ethyl isostearate, cetyl ricinoleate, isononyl isononanoate, isohexadecane, lanolin, lanolin esters, cholesterol, pyrrolidone carboxylic acid/salt (PCA), trimethyl glycine (betaine), tranexamic acid, amino acids (e.g., serine, alanine, threonine, histidine) and/or their salts, panthenol and its derivatives, collagen, hyaluronic acid, elastin, hydrolysates, primrose oil, jojoba oil, epidermal growth factor, soybean saponins, mucopolysaccharides, and mixtures thereof may be used. Other suitable additives or skin actives are discussed in further detail in PCT application WO 97/39733, published Oct. 30, 1997, to Oblong et al., previously incorporated by reference in its entirety.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

Preparation of Osage Orange Extract

A 14 ounce Osage orange fruit was placed into a Waring Juicer and 7 ounces of the liquid contents of the fruit was extracted and removed from the pulp. The juice was a viscous, sticky, aqueous mixture which contains the prenylated isoflavonoids osajin and pomiferin along with additional proteins, antioxidants, polysaccharides, acids, alkaloids, vitamins and enzymes common to the plant. The extract was further diluted with water and a portion of water insoluble components was removed by fractionation of the two incompatible phases which developed upon dilution. The water-soluble components were filtered through diatomaceous earth, followed by filtration through a 0.2 micrometer filter. This formed the basis of an extract of Osage orange containing pomiferin and osajin useful for topical applications.

Example 2

HPLC Analysis of Osage Orange Extract from Example 1

Sample Preparation

Osage orange extract taken from Example 1 was mixed with additional water in a closed container using a magnetic stirring bar at room temperature for 18-24 hours. The weight ratio of Osage orange extract to extraction solvent was 1:4. The mixed material was centrifuged at 100 rpm for 15 minutes in a Clay Adams DYNAC centrifuge from Becton Dickinson, and the liquid extract was collected. Alternatively, the mixture can be clarified by filtration.

The collected liquid extract was diluted in mobile phase solution, filtered through 0.2 μm syringe filter, and injected for HPLC analysis. For HPLC analysis purposes, the aqueous extract created above was further diluted by a factor of 2.

HPLC Analysis Conditions

A Waters 2695 Separation Module equipped with a photodiode array (PDA) 996 detector and Empower software was used for the HPLC analysis. External reference standard of osajin and pomiferin were purchased from Gaia Chemical Corporation in Gaylordsville, Conn. The standard materials were dissolved in mobile phase solution at concentrations as indicated and filtered through 0.2 μm syringe filter prior to injection. A 10 μl of injected material, either standard solution or diluted liquid extract, was chromatographed on a Waters XTerra MS C18 column, 4.6×250 mm, for 25 minutes under 25° C. using isocratic elution at a flow rate of 1.0 ml/min with a mobile phase solution constituting 30% A and 70% B, where A is 1% (w/w) acetic acid in water; and B is acetonitrile. All reagents are of HPLC grade. The detection was at 273.5 nm.

HPLC Test Results

Figure 2:
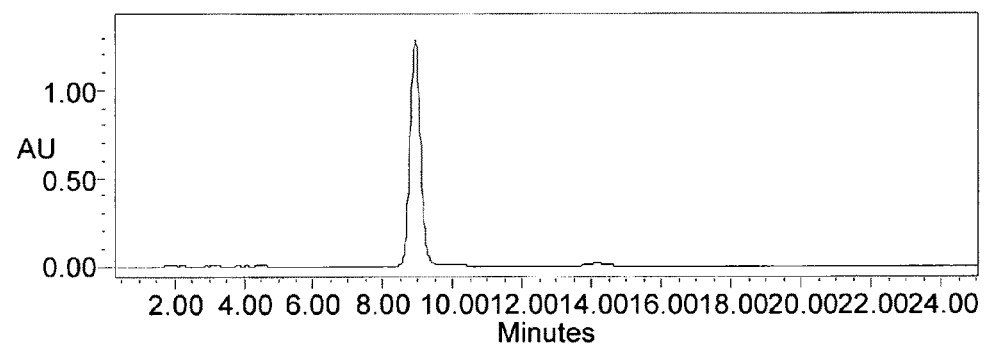
FIG. 2 is a graph showing HPLC analysis results of pomiferin standard.
Figure 3:
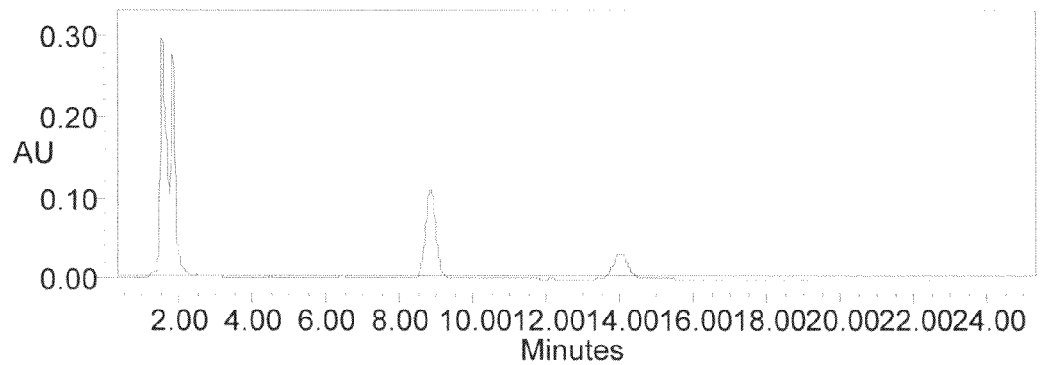
FIG. 3 is a graph showing HPLC analysis results of osage orange aqueous extract.

Preliminary HPLC Analysis Results of Osage Orange Extract
1. Osajin Standard, 420 ug/ml (FIG. 1)
2. Pomiferin Standard, 500 ug/ml (FIG. 2)
3. Osage Orange Aqueous Extract, 2× dilution (FIG. 3)

Example 3

Testing the Influence of Pomiferin Using Human Gene Microarrays On Normal Human Dermal Fibroblasts Methods Cell Culture Normal human dermal fibroblasts were grown in culture flasks until confluent using appropriate culture conditions. Upon reaching confluency the cells will be treated with culture media supplemented with pomiferin at 0.05% which was the maximum level of pomiferin that could be completely dissolved in the culture media without the use of other solvents such as dimethylsulfoxide (DMSO). A separate flask of cells was treated with culture media alone and acted as an untreated control. After applying the test material the cells the cells were incubated for 24 hours at 37±2° C. and 5±1% $CO_2$. At the end of the incubation period the culture media was removed via aspiration and the cells were washed once with cold phosphate buffered saline. After removing the wash the cells they were lysed by adding 700 μl of guanidinium thiocyanate lysis solution. The cell lysate was stored at −75° C. until the RNA extraction process could be completed (see below).

RNA Isolation (Ambion RNAqueous Kit)

To the cell lysates prepared above, an equal volume of 64% ethanol was added and the tubes were vortexed. After combining, up to 700 μl of the mixture was transferred to a glass fiber filter cartridge, and the cartridge was loaded into a 1.5 ml collection tube and the cartridge was centrifuged for 1 minute at 14,000 RPM. The flow through was discarded and any remaining mixture was loaded into the filter cartridge and the centrifugation process was repeated until all of the mixture had been processed. The filter was then washed to remove any residual cellular debris from the RNA bound to the glass fibers by subsequently applying 700 μl of wash solution 1 (1 time) and 500 μl of wash solution 2 (2 times) to the filter cartridge and centrifuging at 14,000 RPM for 1 minute to pass each wash through the cartridge. After each wash the flowthrough was discarded. After the final wash one final spin was performed without wash solution to remove any residual wash solution in the filter cartridge. The RNA bound to the glass fibers within the cartridge was eluted by applying 30 μl of Tris-EDTA buffer (10 mM Tris-HCl, 1 mM EDTA, preheated to 70-80° C.) to the cartridge and centrifuging the cartridge in a new collection tube at 14,000 RPM for one minute. The elution process was repeated with an additional 30 μl of preheated TE buffer. After the RNA was eluted its concentration was quantified using a Ribogreen assay.

RNA Concentration Assay (Molecular Probes Ribogreen Assay)

The Ribogreen reagent was provided as a stock solution in DMSO. Prior to use the reagent was diluted 2000 fold in TE buffer. The RNA assay required 200 μl of diluted Ribogreen reagent per sample to be tested and 1 ml of the reagent for the standards. The diluted reagent was stored protected from light. A series of RNA standards was prepared by diluting purified ribosomal RNA derived from E. coli to the following concentrations: 2 μg/ml, 1 μg/ml, 200 ng/ml, 40 ng/ml and 0 ng/ml (blank). Prior to assaying, the RNA samples prepared above were diluted 1000 fold in TE buffer. For the RNA assay, 100 μl of the diluted samples or standards was transferred to the wells of a 96-well plate. The samples and standards were assayed in duplicate. After the samples/standards were added to the plate, 100 μl of the diluted Ribogreen assay reagent was added to the wells and the plate was gently mixed and allowed to incubate for 5-10 minutes protected from the light. After this incubation the plate was read with a fluorometer using an excitation wavelength of 500 nm and an emission wavelength of 525 nm.

mRNA Amplification (Ambion MessageAmnp aRNA kit)

First Strand cDNA Synthesis: To start the first strand synthesis, 5 μg of total RNA for each sample was added to 600 μl PCR tubes and the total volume of liquid in the tube was adjusted to 12 μl with DEPC $H_2O$. To each tube, 1 μl of T7 Oligo(dT) primer was added and the tube was incubated at 70±2° C. for 10 minutes to denature the RNA and then placed on ice to allow the primer to anneal to the poly A ends of the mRNA. After cooling 2 μl of 10× first strand buffer, 1 μl of RNAse inhibitor and 4 μl of dNTP Mix were added to each tube, and each tube was placed at 42° C. 1 µl of Reverse Transcriptase was added and the tubes were heated and maintained at 42±2° C. for 2 hours. At the end of the two hours the tubes were briefly centrifuged to collect all of the fluid at the bottom of the tube and then placed on ice.

Second Strand Synthesis and cDNA Purification: For the synthesis of the second strand of cDNA the following items were added to the tubes above (in this order): 63 µl DEPC $H_2O$, 10 µl 10× second strand buffer, 4 µl dNTP mix, 2 µl DNA Polymerase and 1 µl of RNAse H. The tube was mixed and then incubated at 16±2° C. for 2 hours. Towards the end of the 2 hour incubation a sufficient quantity of DEPC $H_2O$ was warmed to 50±2° C. and a cDNA purification filter cartridge was equilibrated with 50 µl of cDNA binding buffer (one cartridge per sample) for at least 5 minutes. After the samples were finished incubating, 250 µl of cDNA binding buffer was added to each tube and thoroughly mixed. The contents of the PCR tube was transferred to the cDNA purification filter cartridge. The cartridge was placed in a collection tube and centrifuged at 10,000 RPM for 1 minute. The flow-through was discarded and 650 µl of cDNA wash solution was added to the cartridge. The cartridge was centrifuged again and the flow-through was discarded, and then centrifuged one last time to ensure that the wash buffer had been completely emptied from the filter. The cDNA was eluted by applying 10 µl of preheated DEPC $H_2O$ to the filter and centrifuging the filter in a new collection tube at 10,000 RPM for one minute. This elution was performed one additional time to give a total volume of 16-18 µl of cDNA solution.

In Vitro Transcription to Synthesize aRNA and aRNA Purification: The in vitro transcription began by adding the following to the cDNA solution: 4 µl each of T7 ATP solution, T7 CTP solution, T7 GTP solution, T7 UTP solution, 4 µl of 10× Reaction buffer, and 4 µl of T7 enzyme mix. The tube was mixed and then incubated at 37±2° C. for 6-14 hours. Towards the end of the incubation a sufficient volume of Elution Solution was warmed to 50-60° C. and an aRNA filter cartridge was equilibrated with 100 µl of aRNA binding buffer for at least 5 minutes. At the end of the incubation period, 350 µl of aRNA binding buffer was added to the sample tubes and thoroughly mixed. An additional 250 µl of absolute ethanol was added to each tube. The mixture was transferred to an aRNA filter cartridge; the cartridge was inserted into a collection tube and centrifuged at 10,000 RPM for 1 minute. The flow-through was discarded and 650 µl of aRNA wash buffer was added to the cartridge followed by centrifuging at 10,000 RPM for one minute. After discarding the flow through the cartridge was spun one final time to remove all traces of the wash buffer. The cartridge was transferred to a new collection tube and 25 µl of prewarmed Elution Solution was added to the cartridge. The cartridge was incubated for 2 minutes at room temperature and then aRNA was eluted by centrifuging for 1 minute at 10,000 RPM. This elution was performed one additional time to give a total volume of 45-50 µl of aRNA solution. The final concentration of the aRNA was determined by the Ribogreen assay described above.

Labeling of aRNA With Fluorescent Dyes (PerkinElmer ASAP RNA Labeling Kit) and Purification of Labeled aRNA Labeling: Two tubes were prepared for the labeling process, one for Cy3 labeling (green) and one for Cy5 labeling (red). To the Cy3 tube was added 2 µg of aRNA prepared from the untreated/control sample (the actual color assignment for each sample is not important, but for consistency we normally use Cy3 for the untreated sample) and add enough DEPC $H_2O$ to bring the total volume up to 4 µl. To the Cy5 tube was added 2 µg of aRNA prepared from the sample treated with the test material and enough DEPC $H_2O$ to bring the total volume up to 4 µl. To both tubes was added 5 µl of ASAP labeling buffer and 1 µl of the specific dye for the tube (Cy3 or Cy5). The tubes were incubated for 15 minutes at 85±2° C. At the end of the 15 minutes the tubes were placed on ice to cool them and then 2.5 µl of ASAP stop solution was added to each tube. The proportion given here was enough for analyzing one microarray chip.

Purification: To purify the labeled aRNA, a microcon YM-30 filter column was inserted into a collection tube and filled with 400 µl of TE buffer. The Cy3 and Cy5 probes were combined (12.5 µl of each) and then added to the microcon filter and thoroughly mixed with the TE buffer. The filter was centrifuged at 12,000 RPM for 8 minutes and the flow-through was discarded. The column was washed twice with 400 µl of TE buffer, and the flow through was discarded each time. After the final wash the filter column was inverted, placed into a new collection tube and centrifuged at 12,000 RPM for 2 minutes to collect the probe (the probe was further concentrated in a volume of 2-30 µl of residual TE buffer).

Microarray Hybridization And Washing (Agilent Technologies Microarrays)

For hybridization, 11 µl of 10× control target RNA (supplied with Agilent Technologies In Situ Hybridization Kit) was mixed with 30 µl of DEPC water and 2.2 µl of 25× Agilent Fragmentation Buffer. This mixture was incubated at 65° C. for approximately 30 minutes in a hybridization oven. At the end of the incubation 55 µl of Agilent Hybridization Buffer was added along with the fluorescent aRNA probes prepared above. An Agilent SUREHYB hybridization chamber was prepared by inserting a glass gasket slide into the bottom half of the chamber. At the end of the incubation, the hybridization mixture (approximately 110 µl) was applied to the glass gasket slide and an Agilent Microarray Chip was placed face down on top of this gasket such that the hybridization solution was sandwiched between the glass gasket slide and the microarray face of the chip. The top half of the chamber was attached and the connecting thumbscrew was tightened. After verifying that there was good bubble formation in the chamber, it was placed into the hybridization oven for approximately 17 hours (65° C. and rotating at 4 RPM). At then end of the hybridization period the microarray/glass gasket were removed from the SUREHYB chamber and placed in 50 ml of wash solution 1 (room temperature, 6×SSC, 0.005% Triton X-102). After the gasket had fallen away from the microarray, the array was transferred to 300 ml of fresh wash solution 1 on a magnetic stir plate. The array was washed while the solution was mixed at medium speed for 10 minutes and then transferred to 300 ml of wash solution 2 (0.1×SSX, 0.005% Triton X-102, 4° C.) for 5 minutes. After the final wash the array was centrifuged at 500 RPM for 5 minutes to dry it.

Microarray Scanning And Analysis

The microarrays were scanned with an Axon GenePix 4100A Scanner with the scanning resolution set to 10 µm and analyzed with GenePix Pro software. During the initial scan the PMT gains for the scanner were adjusted such that the cy5/cy3 image count ratios are between 0.88 and 1.12.

Calculations

RNA Ribogreen Assay

To derive the standard curve for the Ribogreen assay, the relative fluorescent units versus the known RNA concentrations in µg/ml for the standards was plotted and subjected to regression analysis to establish the line that best fits these data points. Mean RFU values for the test materials and untreated samples was used to estimate the amount of RNA present in each sample.

Microarray Calculations

The level of gene expression is related to the fluorescence intensity of the probed gene marker on the microarray. Since it is possible to have differences in labeling efficiency when making the Cy3 and Cy5 probes it is essential to normalize the fluorescence measurements between the two respective dyes before looking at changes in gene expression. Fluorescence intensities for the microarrays were subjected to global normalization. The total fluorescent signal for both dyes was normalized with a correction factor that made the ratio of total intensities for both dyes equal to one.

After normalizing the fluorescence measurements it was possible to look for changes in gene expression. Criteria for evaluating changes in gene expression typically require the following three criteria:
1. The ratio of Cy3/Cy5 (untreated/treated) fluorescence intensity is greater than 1.3 or less than 0.7. This relates to a change in gene expression of at least +/−30%
2. The fluorescence intensity of the gene marker is greater than the background intensity.
3. The gene feature is clearly marked specifically by the aRNA probes and is not due to non-specific fluorescence (i.e. SDS streaks will leave fluorescent trails).

The first two criteria can be filtered via computer analysis of the data. The last criterion requires a visual inspection of the array spot to confirm.

Results

In the studies reported below, Cy3/Cy5 would be equivalent to F635/F532 and the fluorescence ratio is identified as the "Ratio of Medians 635/532". The 1D1 and Name identify the gene and its location on the human genome.

The results of treatment of normal human dermal fibroblasts with 0.05% purified pomiferin showing Type 1A1 Collagen gene expression (COL1A1) are provided in Table 1.

TABLE 1

Gene expression for Type 1A1 Collagen results from treatment of normal human dermal fibroblasts with 0.05% Pomiferin.
Fib Pom Scan 2

| ID1 | Name | F532 Median | F635 Median | Ratio of Medians (635/532) | GeneName | Description |
|---|---|---|---|---|---|---|
| 13677 | I_960109 | 15785 | 38576 | 2.446 | COL1A1 | Alpha 1 subunit of type I collagen, a structural constituent of bone, involved in skeletal development and epidermal differentiation |

The results of treatment of normal human dermal fibroblasts with purified pomiferin showing Elastin gene expression (ELN) are provided in Table 2.

TABLE 2

Gene expression for Elastin (ELN) results from treatment of normal human dermal fibroblasts with 0.05% Pomiferin
Fib Pom Scan 2

| ID1 | Name | F532 Median | F635 Median | Ratio of Medians (635/532) | GeneName | Description |
|---|---|---|---|---|---|---|
| 4785 | I_930697 | 1830 | 3010 | 1.651 | ELN | Elastin, component of arterial, skin, and lung extracellular matrices |

Example 4

Examination of Pomiferin's Influence on Collagen 1A1 and Elastin Protein Expression Using ELISA Assays Methods Preparation of Fibroblasts Normal human dermal fibroblasts were seeded into the individual wells of a 12 well plate in 1.0 ml of Fibroblast Growth Media (FGM) and incubated overnight at 37±2° C. and 5±1% $CO_2$. On the following day the media was removed via aspiration to eliminate any non-adherent cells and replaced with 1.0 ml of fresh FGM. The cells were grown until confluent, with a media change every 48 to 72 hours. Upon reaching confluency the cells were treated for 24 hours with DMEM supplemented with 1.5% FBS to wash out any effects from the growth factors included in the normal culture media. After this 24-hour wash out period the cells were treated with the test materials at the specified concentrations dissolved in DMEM with 1.5% FBS. Ascorbic acid and retinol were used as a positive controls for collagen synthesis. Untreated cells (negative controls) just received DMEM with 1.5% FBS. The cells were incubated for 48 hours and at the end of the incubation period cell culture medium were collected and either stored frozen (−75° C.) or assayed immediately. Materials were tested in triplicate.

MTT Assay

After the 2-day incubation, the cell culture medium was removed (see above) and the fibroblasts were washed twice with PBS to remove any remaining test material. After the final wash, 1 ml of media supplemented with 0.5 mg/ml MTT was added to each well and the cells were incubated for 1 hour at 37±2° C. and 5±1% $CO_2$. After the incubation, the MTT solution was removed and the cells were washed again once with PBS and then 1 ml of isopropyl alcohol was added to the well to extract the purple formazin crystals. Two hundred microliters of the isopropyl extracts was transferred to a 96-well plate and the plate was read at 540 nm using isopropyl alcohol as a blank.

Procollagen Assay (Takara ELISA Kit)

A series of type I C-peptide standards was prepared ranging from 40 ng/ml to 640 ng/ml. An ELISA microplate was prepared by removing any unneeded strips from the plate frame. In each well to be used 100 µl of peroxidase-labeled anti procollagen type I-C peptide was added, followed by 20 µl of either sample or standard. The microplate was covered and allowed to incubate for 3±0.25 hours at 37° C. After the incubation each well was washed three times with 400 µl of wash buffer. After the last wash was removed 100 µl of peroxidase substrate solution (hydrogen peroxide+tetramethylbenzidine as a chromagen) was added to each well and the plate was incubated for 15±5 minutes at room temperature. After the incubation 100 µl of stop solution (1 N sulfuric acid) was added to each well and the plate was read using a microplate reader at 450 nm.

Elastin ELISA Plate Preparation

Soluble α-elastin was dissolved in 0.1 M sodium carbonate (pH 9.0) at a concentration of 1.25 µg/ml. 150 µl of this solution was applied to the wells of a 96-well maxisorp Nunc plate and the plate was incubated overnight at 4° C. On the following day the wells were saturated with PBS containing 0.25% BSA and 0.05% Tween 20. The plate was incubated with this blocking solution for 1 hour at 37° C. and then washed two times with PBS containing 0.05% Tween 20.

Elastin Competitive ELISA

A set of α-elastin standards was generated ranging from 0 to 100 ng/ml. 180 µl of either standard or sample was transferred to a 650 µl microcentrifuge tube. An anti-elastin antibody solution was prepared (the antibody will be diluted 1:100 in PBS containing 0.25% BSA and 0.05% Tween 20) and 20 µl of the solution was added to the tube. The tubes were incubated overnight at 4±2° C. On the following day, 150 µl was transferred from each tube to the 96-well elastin ELISA plate and the plate was incubated for 1 hour at room temperature. The plate was washed 3 times with PBS containing 0.05% Tween 20. After washing, 200 µl of a solution containing a peroxidase linked secondary antibody (1:2500) diluted in PBS containing 0.25% BSA and 0.05% Tween 20 was added, and the plate was incubated for 1 hour at room temperature. After washing the plate three times as described above, 200 µl of a substrate solution was added and the plate was incubated for 10 to 30 minutes in the dark at room temperature. After this final incubation the plate was read at 460 nm using a plate reader.

Calculations

MTT Assay

The mean MTT absorbance value for the negative control cells were calculated and used to represent 100% value for cell number. The individual MTT values from the cells undergoing the various treatments were divided by the mean value for the negative control cells and expressed as a percent to determine the change in cell number caused by each treatment. If the MTT assay demonstrated a reduction in cell viability of greater then 10%, the test was considered invalid. In the assay with pomiferin, the MTT assay demonstrated cell survivals of 100% at all concentrations tested Procollagen And Elastin Concentrations To quantify the amount of procollagen and elastin present, a standard curve was generated using known concentrations of each substance provided by the manufacturers of the test kits. A regression analysis was performed to establish the line that best fits these data points. Absorbance values for the unknown samples were used to estimate the amount of procollagen and elastin present in each sample.

Fibrillin Expression

Fibrillin Immunodetection

A PVDF membrane was prewet in methanol, equilibrated with TBS (TBS: 20 mM Tris, pH 7.5, 150 mM NaCl) and assembled into the Bio-Dot microfiltration apparatus. After assembly, 100 µl of TBS was added to the wells in the Bio-Dot and the vacuum was applied to ensure that there was an adequate flow through all of the wells. Next, 250 µl of each media sample was assigned a well in the apparatus and the sample was applied to the appropriate well. After all of the samples had been added, a vacuum was applied to the apparatus to draw the fluid of the samples through the membrane, leaving the protein adhered to the membrane. TBS was added to wells not assigned a sample to ensure that the membrane did not dry out during the procedure. At the end of the blotting procedure the membrane was removed from the Bio-Dot apparatus, washed in TBS for 5-10 minutes and then placed into blocking solution (TBS with 1% non-fat milk powder) and allowed to incubate for at least 1 hour at room temperature on a rocking platform.

Antibody Incubation and Detection

After blocking, the membrane was transferred to 20 ml of TBST (TBS with 0.1% Tween-20) and 0.1% non-fat powdered milk with an appropriate dilution of antibody and allowed to incubate overnight at 4° C. on a rocking platform. After this incubation the membrane was washed 3 times (1× for 15 minutes and 2x for 5 minutes) in TBST. The secondary antibody (conjugated with a fluorophore) was then incubated with the membrane in 15 ml of TBST with 0.1% non-fat powdered milk for 1 hour at room temperature and then washed 3 times with TBS (1×15 minutes, 2× for 5 minutes).

After the final wash, the membrane was placed into a BioRad Molecular Imager FX and scanned using an excitation laser and emission filter combination appropriate for the fluorophore. Images produced by the scanner were then analyzed using ImageJ image analysis software.

Calculations

MTT Assay

The mean MTT absorbance value for the negative control cells was calculated and used to represent 100% cell viability. The individual MTT values from the cells undergoing the various treatments were then divided by the mean value for the negative control cells and expressed as a percent to determine the change in cell viability caused by each treatment.

Image Analysis

Fluorescence intensity measurements were expressed in Relative Fluorescence Units (RFU). Mean RFU values for each treatment were then calculated and treatments were compared using a one way ANOVA.

Results

Figure 4:
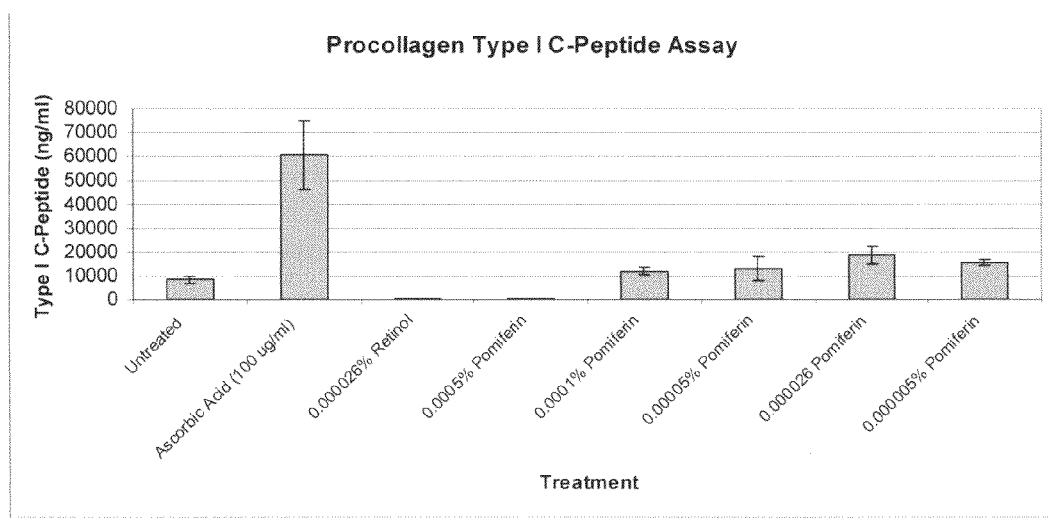
FIG. 4 is a graph showing the results of treatment of normal human dermal fibroblasts with various concentrations of pomiferin on Type 1A1 Procollagen expression.

Results of treatment of normal human dermal fibroblasts with various concentrations of pomiferin on Type 1A1 Procollagen expression are shown in FIG. 4.

Figure 5:
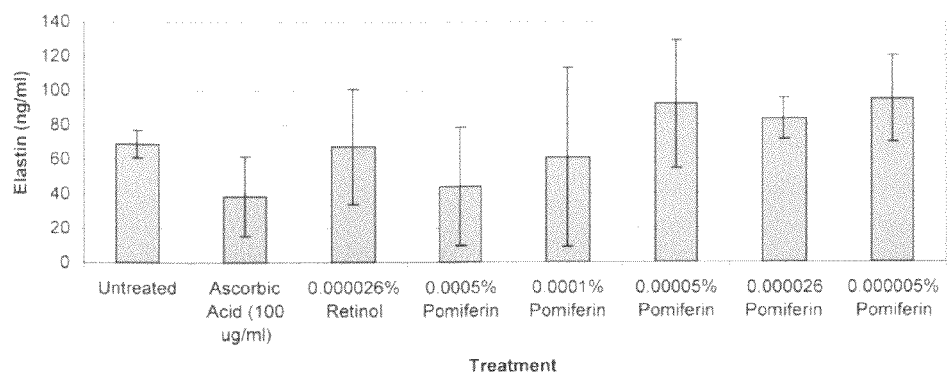
FIG. 5 is a graph showing the results of treatment of normal human dermal fibroblasts with various concentrations of pomiferin on Elastin expression.

Results of treatment of normal human dermal fibroblasts with various concentrations of pomiferin on Elastin expression are shown in FIG. 5.

Figure 6:
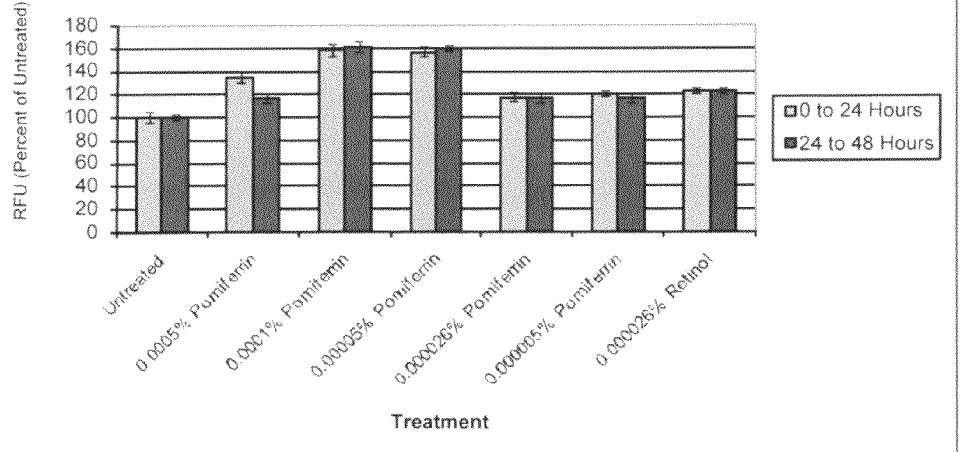
FIG. 6 is a graph showing results of treatment of normal human dermal fibroblasts with various concentrations of pomiferin on Fibrillin expression.

Results of treatment of normal human dermal fibroblasts with various concentrations of pomiferin on Fibrillin expression are shown in FIG. 6.

Example 5

Oil-in-water Emulsions

The osage orange extract from Example 1 was formulated into an oil-in-water emulsion using the following formulation and process:

15

Oil in Water Emulsion containing Osage orange extract

| Ingredient | INCI Nomenclature | % |
| --- | --- | --- |
| Water | Water | q.s |
| Versene 100 | Tetrasodium EDTA | 0.10 |
| Glycerin | Glycerin | 2.00 |
| Carbopol Ultrez 10 | Carbomer | 0.20 |
| Brookswax D | Cetearyl Alcohol & Ceteareth-20 | 2.00 |
| Liquiwax DIADD** | Dioctyldodecyl Dodecanedioate | 5.00 |
| Loronate TMP-TC | Trimethylolpropane Tricaprylate/Tricaprate | 2.00 |
| Arlacel 60 | Sorbitan Stearate | 1.50 |
| Stearyl Alcohol | Stearyl alcohol | 0.20 |
| Cetyl Alcohol | Cetyl Alcohol | 0.50 |
| Stearic Acid | Stearic Acid | 0.50 |
| Myritol 318 | Caprylic/Capric Triglyceride | 2.00 |
| DC 200/100 cst | Dimethicone | 0.75 |
| Water | Water | 5.00 |
| TEA 99 | Triethanolamine | 0.25 |
| Osage Orange Extract | — | 1.00 |
| Mikrokill COS | Phenoxyethanol & Caprylyl Glycol & Chlorphenesin | 0.75 |

Procedure:
1. Combine Phase A and heat to 75° C. Mix until uniform.
2. Combine Phase B and heat to 75° C. Mix until uniform.
3. With slow mixing, add Phase B to Phase A. Mix for 20 minutes.
4. Add pre-mix Phase C and mix until uniform. Turn off the heat.
5. In side kettle pre-mix Phase D and add to the batch below 40° C. Mix until uniform.
6. Add Mikrokill COS and fragrance of Phase E, and mix until uniform.

Example 6

Water-in-oil Emulsions

The osage orange extract from Example 1 was formulated into a water-in-oil emulsions using the following formulation and process:

Water in Oil Emulsion containing Osage orange extract

| Ingredient | INCI Nomenclature | % |
| --- | --- | --- |
| Water | Water | q.s to 100 |
| Glycerin | Glycerin | 3.00 |
| Sodium Chloride | Sodium Chloride | 1.00 |
| Osage orange Extract | | 1.00 |
| Mikrokill COS | Phenoxyethanol & Caprylyl Glycol & Chlorphenesin | 0.75 |
| SF1328 | Cyclomethicone & Dimethicone Copolyol | 10.00 |
| SF 1202 | Cyclomethicone | 8.50 |
| Gel Base Sil | Cyclomethicone & Dimethicone | 1.50 |
| Gel Base BSM-PE | Cyclomethicone & Dimethicone & Phenyl Trimethicone & Polyethylene | 1.50 |
| | | 100.00 |

Procedure:
1. Mix all ingredients of Phase A together.
2. Combine Phase B ingredients in order shown, thoroughly mixing each component until homogeneous before adding the next ingredients.
3. Slowly add Phase A to Phase B with good mixing. Gradually increase agitation to high shear as mixture thickens. Continue agitation for 10 minutes.

16

Example 7

Eye Gel Compositions

The Osage orange extract from Example 1 was encapsulated into a liposomal composition, then the encapsulated Osage orange extract was incorporated into an eye gel composition using the following process:

EYE GEL containing Osage orange liposome

| Ingredient | INCI Nomenclature | % |
| --- | --- | --- |
| Water | Water | Q.S |
| Carbopol Ultrez 21 | Acrylates/C10-30 Alkyl Acrylate Crosspolymer | 0.50 |
| Keltrol CG-SFT | Xanthan Gum | 0.10 |
| Butylene Glycol | Butylene Glycol | 5.00 |
| Mikrokill COS | Phenoxyethanol & Caprylyl Glycol & Chlorphenesin | 1.00 |
| Dow Corning 193 Surfactant | Dimethicone Copolyol | 0.30 |
| Disodium EDTA | Disodium EDTA | 0.10 |
| AMP 95 | Aminomethylpropanol | 0.45 |
| Osage orange liposome | | 1.00 |

Procedure:
1. Disperse the Carbopol Ultrez 21 in water at 50° C. and add the Keltrol CG-SFT. Mix until uniform.
2. Add the Butylene Glycol, Mikrokill COS, AMP, EDTA and Silicone 193. Mix until uniform.
3. Add the Osage orange liposome with sweep agitation at 40° C. Mix until uniform.
4. Adjust pH to 5.5 if necessary.

Example 8

Encapsulated Osage Orange Extract

The Osage orange from Example 1 was encapsulated into a polymeric matrix using the techniques outlined in US Patent Publication No. 2003/0198682 A1. The publication is incorporated by reference in its entirety herein.

Example 9

Lipstick Compositions

The Osage orange extract encapsulated in the polymeric matrix of Example 8 was formulated into a lipstick using the following formulation and process:

LIPSTICK containing Osage orange extract

| Ingredient | INCI Nomenclature | % |
| --- | --- | --- |
| Phase (A) | | |
| Castor Oil | *Ricinus Communis* (Castor) Seed Oil | 32.45 |
| Schercemol TISC | Triisostearyl Citrate | 15.00 |
| Liquiwax PolyIPL | Stearyl PPG-3 Myristyl Ether Dimer Dilinoleate | 5.00 |
| Liquiwax PolyEFA | Octyldodecyl PPG-3 Myristyl Ether Dimer Dilinoleate | 15.00 |
| Candelilla Wax | *Euphorbia Cerifer* (Candelilla) Wax | 6.00 |
| Ozokerite 170D | Ozokerite | 2.50 |

LIPSTICK containing Osage orange extract

| | INCI Nomenclature | % |
|---|---|---|
| Microwax SP 19 | Microcrystalline Wax | 3.50 |
| Carnauba Wax | Copernicia cerifera (carnauba) wax | 1.50 |
| Methylparaben | Methylparaben | 0.20 |
| Propylparaben | Propylparaben Phase (B) | 0.10 |
| Color Grind | | |
| Red 7 Lake c19-7711 | Red 7 Lake | 0.04 |
| Red 6 Lake c19-7712 | Red 6 Lake | 0.17 |
| Red Iron Oxide A-1205 | Iron Oxides | 2.00 |
| Titanium Dioxide Ultra Fine 70110 | Titanium Dioxide | 2.00 |
| Black Iron Oxide c33-134 | Iron Oxides | 0.05 |
| Liquiwax PolyEFA* | Octyldodecyl PPG-3 Myristyl Ether Dimer Dilinoloeate Phase (C) | 4.44 |
| Ascorbyl Palmitate | Ascorbyl Palmitate | 0.05 |
| Flamenco Red | Mica and Titanium Dioxide | 10.00 |
| Osage orange extract powder | | 1.00 |

Procedure:
1. Combine Waxes, Oils and Preservatives (Phase A) and heat to 83°-87° C.
2. Hold temperature and stir until homogeneous.
3. Drop temperature to 75°-80° C., and add Phase B; mix until homogeneous
4. Add Pearl, Osage orange extract and Ascorbyl Palmitate (Phase C).
5. Pour into molds.

Example 10

Toner Compositions

The Osage orange extract of Example 1 was formulated into an aqueous alcoholic tonic using the following formulation and process:

Toner containing Osage orange extract

| Ingredient | INCI Nomenclature | % |
|---|---|---|
| Water | Water | Qs. To 100 |
| Betafin BP-20* | Betaine | 3.00 |
| Osage orange extract | | 1.00 |
| Witch Hazel w/14% Alcohol | Water & Ethanol & Witch Hazel | 25.00 |
| Mikrokill COS | Phenoxyethanol & Caprylyl Glycol & Chlorphenesin | 0.75 |

Procedure:
  Charge Water and add Betafin BP-20, and Osage orange extract. Mix until uniform.
  Add Witch Hazel and Mikrokill COS, mix until uniform.

Example 11

Body Wash Compositions

The osage orange extract of Example 1 was formulated into a body wash using the following formulation and process.

Body Wash containing Osage orange extract

| Ingredient | INCI Nomenclature | % |
|---|---|---|
| Water | Water | Q.S |
| Hamp-ene Na2 | Disodium EDTA | 0.10 |
| Glycerin | Glycerin | 2.00 |
| Standapol WAQ-Special | Sodium Lauryl Sulfate | 30.00 |
| Standapol ES-2 | Sodium Laureth Sulfate | 25.00 |
| Cerasynt IP | Glycol Stearate & Stearic Acid & Aminomethyl Propanol | 0.50 |
| Velvetex BA-35 | Cocoamidopropyl Betaine | 7.00 |
| Cocamide MEA | Cocamide MEA | 2.00 |
| Mikrokill COS | Phenoxyethanol & Caprylyl Glycol & Chlorphenesin | 0.75 |
| Osage orange extract | | 1.00 |

Procedure:
1. Heat Water to 70° C. and add Disodium EDTA, Glycerin, and mix until uniform.
2. Keep temperature above 70° C. and add Standapol WAQ Special, Standapol ES-2, Cerasynt IP, Cocamide MEA, Velvetex BA-35, and mix until uniform.
3. Cool to 45° C. and add Mikrokill COS and Osage orange extract.
4. Mix until homogenous.

Example 12

Yeast/Osage Orange Ferment Products

The osage orange extract from Example 1 was included as part of a fermentation media containing the Yeast *Saccharomyces cerevisiae*. A sample of the extract from Example 1 was placed into an aqueous mixture of Baker's Yeast growth media obtained from Red Star Yeast (Milwaukee, Wis.). The media was inoculated with an active *Saccharomyces cerevisiae* yeast culture also obtained from Red Star and the mixture was allowed to ferment under controlled aerobic conditions to provide a Live Yeast Cell Derivative (LYCD) obtained using stress conditions as described in U.S. Pat. No. 2,239,345.

Example 13

Sub-micron Emulsion Concentrates

This example illustrates a sub-micron emulsion concentrate that contains an osage orange extract prepared as described in Example 1.

| Ingredient | Wt % |
|---|---|
| Trimethylolpropane Tricaprylate/Tricaprate | 18.0 |
| Glycerin | 8.0 |
| Cetearyl alcohol | 2.0 |
| Ceteareth 20 | 2.0 |
| Glyceryl stearate | 2.0 |
| BHT | 0.01 |
| Osage Orange Extract | 1.0 |
| Water | to 100 |

What is claimed is:
1. A method for regulating skin condition comprising topically applying to skin a composition comprising Maclura pomifera (Osage orange) fruit extract encapsulated in a delivery vehicle, wherein said delivery vehicle is selected from the group consisting of a liposome, a maltodextrin, a polymeric matrix, a niasome and a nanoparticle, wherein said fruit extract is present in an amount of from about 0.0000001% to about 10% based on the total weight of the composition, wherein said application improves the appearance and condition of the skin by upregulating collagen 1A1 and elastin gene expression in normal human dermal fibroblasts, wherein said fruit extract comprises prenylated isoflavonoids.

2. The method of claim 1 wherein said fruit extract is present in an amount of from about 0.00001% to about 1% based on the total weight of the composition.

3. The method of claim 1 wherein said fruit extract is present in an amount of from about 0.01% to about 1% based on the total weight of the composition.

4. A method for regulating skin condition comprising topically applying to skin a composition containing:
   (a) a safe and effective amount of prenylated isoflavonoid sufficient for increasing collagen 1A1 and elastin gene expression in normal human dermal fibroblasts wherein said prenylated isoflavonoid is selected from the group consisting of pomiferin, osajin and a combination thereof; and
   (b) a cosmetically or dermatologically acceptable carrier for said prenylated isoflavonoid; wherein said prenylated isoflavonoid is present in an amount of from about 0.0000001% to about 10% based on the total weight of the composition, and wherein said carrier is present in an amount of from about 50% to about 99% based on the total weight of the composition;
   wherein said application improves the appearance and condition of the skin by upregulating collagen 1A1 and elastin gene expression in normal human dermal fibroblasts.

5. The method of claim 4 wherein said prenylated isoflavonoid is isolated from a botanical extract.

6. The method of claim 5 wherein said botanical extract is from Maclura pomifera (Osage orange).

7. The method of claim 4 wherein said prenylated isoflavonoid is present in an amount of from about 0.01% to about 1% based on the total weight of the composition.

8. The method of claim 4 wherein said composition further comprises one or more skin actives.

9. The method of claim 4 wherein said prenylated isoflavonoid is present in an amount of from about 0.00001% to about 1% based on the total weight of the composition.

10. The method of claim 4 wherein said prenylated isoflavonoid is present in an amount of from 0.0001% to 0.05% based on the total weight of the composition.

11. A composition comprising a Maclura pomifera (Osage orange) fruit extract encapsulated in a delivery vehicle, wherein said delivery vehicle is selected from the group consisting of a liposome, a maltodextrin, a polymeric matrix, a niosome, and a nanoparticle, wherein said fruit extract is effective to increase collagen 1A1 and elastin gene expression in normal human dermal fibroblasts, and wherein said fruit extract is present in an amount of from about 0.0000001% to about 10% based on the total weight of the composition, wherein said fruit extract comprises prenylated isoflavonoids.

12. The composition of claim 11 wherein said fruit extract is present in an amount of from about 0.00001% to about 1% based on the total weight of the composition.

13. The composition of claim 11 wherein said fruit extract is present in an amount of from about 0.01% to about 1% based on the total weight of the composition.

* * * * *